United States Patent
Bullwinkel et al.

[11] Patent Number: 5,669,900
[45] Date of Patent: Sep. 23, 1997

[54] SPUNBOND LOOP MATERIAL FOR HOOK AND LOOP FASTENING SYSTEMS

[75] Inventors: Edward Paul Bullwinkel, Roswell; Leon Eugene Chambers, Jr., Cumming; Robert Gillette Geer, Canton; Jay Sheldon Shultz, Roswell, all of Ga.

[73] Assignee: Kimberly-Clark Worldwide, Inc., Irving, Tex.

[21] Appl. No.: 333,803

[22] Filed: Nov. 3, 1994

Related U.S. Application Data

[63] Continuation-in-part of Ser. No. 148,078, Nov. 3, 1993, Pat. No. 5,538,019.

[51] Int. Cl.$^6$ .................................................. A61F 13/15
[52] U.S. Cl. ........................... 604/391; 24/447; 24/450; 128/DIG. 15; 604/386; 604/393; 604/400; 604/402; 428/100
[58] Field of Search ................................. 131/331, 332, 131/345; 24/442, 445, 447, 450; 604/391, 386, 393, 400, 402; 128/DIG. 15; 428/100

[56] References Cited

U.S. PATENT DOCUMENTS

| | | |
|---|---|---|
| 3,397,700 | 8/1968 | Harlow et al. . |
| 3,667,478 | 6/1972 | Waterbury . |
| 3,704,192 | 11/1972 | Soehngen et al. . |
| 4,729,391 | 3/1988 | Woods et al. . |
| 4,903,714 | 2/1990 | Barnes et al. ........................ 131/335 |
| 5,012,829 | 5/1991 | Thesing et al. . |
| 5,032,122 | 7/1991 | Noel et al. ........................... 24/442 X |
| 5,058,245 | 10/1991 | Saito ................................... 24/442 X |
| 5,176,670 | 1/1993 | Roessler et al. ..................... 604/391 |
| 5,374,262 | 12/1994 | Keuhn, Jr. et al. ................. 604/391 |
| 5,386,595 | 2/1995 | Kuen et al. ......................... 24/442 X |
| 5,403,302 | 4/1995 | Roessler et al. ..................... 604/391 |
| 5,423,789 | 6/1995 | Kuen ................................. 604/391 X |
| 5,476,702 | 12/1995 | Datta et al. ........................ 604/391 X |
| 5,498,461 | 3/1996 | Rockney ............................. 24/442 X |

FOREIGN PATENT DOCUMENTS

| | | |
|---|---|---|
| 0604731 | 7/1994 | European Pat. Off. . |
| 2009251 | 1/1970 | France . |
| 922698 | 4/1963 | United Kingdom . |
| 9220251 | 11/1992 | WIPO . |

OTHER PUBLICATIONS

Japanese Abstract JP,A,06 033 359 dated Feb. 8, 1994.

*Primary Examiner*—Jennifer Bahr
*Attorney, Agent, or Firm*—William D. Herrick

[57] ABSTRACT

A loop material for a hook and loop fastening system composed of: 1) a backing material; and 2) a layer of a nonwoven spunbond web attached to the backing material, the nonwoven spunbond web comprising a plurality of continuous intertwined filaments, each having a diameter of about 25 to about 100 microns, the plurality of filaments laid randomly to define a plurality of intertwined loop springs, each having a diameter of about 0.5 to about 3 millimeters.

16 Claims, 2 Drawing Sheets

SPUNBOND LOOP MATERIAL FOR HOOK AND LOOP FASTENING SYSTEMS

This application is a continuation-in-part of U.S. patent application Ser. No. 08/148,078 filed Nov. 3, 1993, now U.S. Pat. No. 5,538,019.

FIELD OF THE INVENTION

The present invention relates to hook and loop fastening systems. More particularly, the present invention relates to a nonwoven web which may be used as a loop portion of a hook and loop fastening system.

BACKGROUND OF THE INVENTION

Hook and loop mechanical fasteners are becoming a widely used material in many products. Many hook and loop materials are used in areas where they are subjected to considerable movement, twisting and turning. One such use is personal care absorbent articles, including baby diapers and incontinence products. Such products are generally single-use items which are discarded after a relatively short period of use—usually in the range of hours. As a result, it is desirable to avoid expensive components in the design of such products. Conversely, these mechanical fasteners must be able to withstand the rigorous use without separation of the hook and loop components. Thus, there must be a balance between economy and utility.

A proposed reason for premature separation of the hook from the loop material is that the number of individual hook and loop engagements is insufficient to provide adequate attachment due to the failure of the loop fibers to maintain a "z" axis orientation (90°) from the surface of the loop material so as to allow the hook elements to engage the loops and promote a greater number of individual hook and loop engagements.

Another proposed reason for premature separation, especially when conventional nonwoven materials are used as loops, is that the loops of the loop material pull out during use leaving fewer hook and loop engagements.

Consequently, there is a need to provide a loop portion for a hook and loop fastener system which is relatively inexpensive. A need exists for a loop portion of a hook and loop fastener system having loop fibers that tend to maintain a "z" axis orientation (90°) from the surface of the loop material. A need also exists for a loop material which has loops that tend to resist pulling out during use.

DEFINITIONS

As used herein, the term "nonwoven web" refers to a web that has a structure of individual fibers or filaments which are interlaid, but not in an identifiable repeating manner. Nonwoven webs have been, in the past, formed by a variety of processes known to those skilled in the art such as, for example, meltblowing, spunbonding and carded web processes.

As used herein, the term "spunbond web" refers to a web of small diameter fibers and/or filaments which are formed by extruding a molten thermoplastic material as filaments from a plurality of fine, usually circular, orifices in a spinnerette with the diameter of the extruded filaments then being rapidly reduced, for example, by non-eductive or eductive fluid-drawing or other well known spunbonding mechanisms. The production of spunbond nonwoven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the terms "thermoplastic material" and "thermoplastic polymer" refer to a long-chain polymer that softens when exposed to heat and returns to its original condition when cooled to room temperature. Exemplary thermoplastic materials include, without limitation, polyvinyl chlorides, polyesters, polyamides, polyfluorocarbons, polyolefins, polyurethanes, polystyrenes, polyvinyl alcohols, caprolactams, copolymers of ethylene and at least one vinyl monomer (e.g., poly(ethylene vinyl acetates), copolymers of ethylene and n-butyl acrylate (e.g., ethylene n-butyl acrylates), and acrylic resins.

As used herein, the term "machine direction" refers to the planar dimension of a nonwoven fibrous web which is in the direction of travel of the forming surface onto which fibers are deposited during formation of the web.

As used herein, the term "cross-machine direction" refers to the planar dimension of a nonwoven fibrous web which is in the direction that is perpendicular to the machine direction defined above.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "consisting essentially of" does not exclude the presence of additional materials which do not significantly affect the desired characteristics of a given composition or product in a negative way. Exemplary materials of this sort would include, without limitation, pigments, antioxidants, stabilizers, surfactants, waxes, flow promoters, particulates or materials added to enhance processability of a composition.

SUMMARY OF THE INVENTION

The present invention addresses the problems described above by providing a loop material for a hook and loop fastening system. The loop material is composed of: 1) a backing material; and 2) a layer of a nonwoven spunbond web attached to the backing material. The nonwoven spunbond web contains a plurality of spunbond fibers or filaments formed to define a plurality of intertwined loop springs. More particularly described, the nonwoven web is made from a plurality of filaments generally having diameters greater than those typically found in spunbond filaments, or greater than about 18-25 microns. The filaments are substantially continuous and intertwined. The filaments are laid randomly onto a moving belt to form a web having a series of interwoven, simple loop springs. Filaments useful in disclosed embodiments have diameters of about 25 to about 100 microns and form intertwined loop springs having diameters of about 0.5-3 millimeters. Desirably, filaments may have diameters of about 25 to about 40 microns and form intertwined loop springs having diameters of about 1-2 millimeters.

Nonwoven spunbond webs with these fiber diameters in the described filament loop configuration are believed to provide openness in combination with desirable characteristics. For example, the above-described nonwoven webs have a level of openness which is thought to permit desirable penetration of mechanical hooks (for hook and loop type fasteners) in combination with a level of resilience and resistance to compression to avoid collapse of the fabric. Additionally, the loops are thought to provide for engagement of mechanical hook fasteners.

As another example, the above-described nonwoven webs have a level of openness which is thought to permit filtration of high volumes of fluids (i.e., liquid and/or gas) without collapse of the fabric.

Generally speaking, the filaments may be formed from a thermoplastic polymer such as, for example, polyolefins, polyamides and polyesters. The polyolefin may be, for example, polyethylene, polypropylene, polybutene, ethylene copolymers, propylene copolymers and butene copolymers.

According to an aspect of the present invention, the loop material may be used as an outer cover for a personal care absorbent product such as, for example, a diaper, training-pant or the like. Desirably, the outer cover is composed of a loop material formed from a backing material and a layer of the nonwoven spunbond web described above. Even more desirably, the backing material of the outer cover is a layer of film or film-like material.

DETAILED DESCRIPTION OF THE PREFERRED EMBODIMENT

Figure 1:
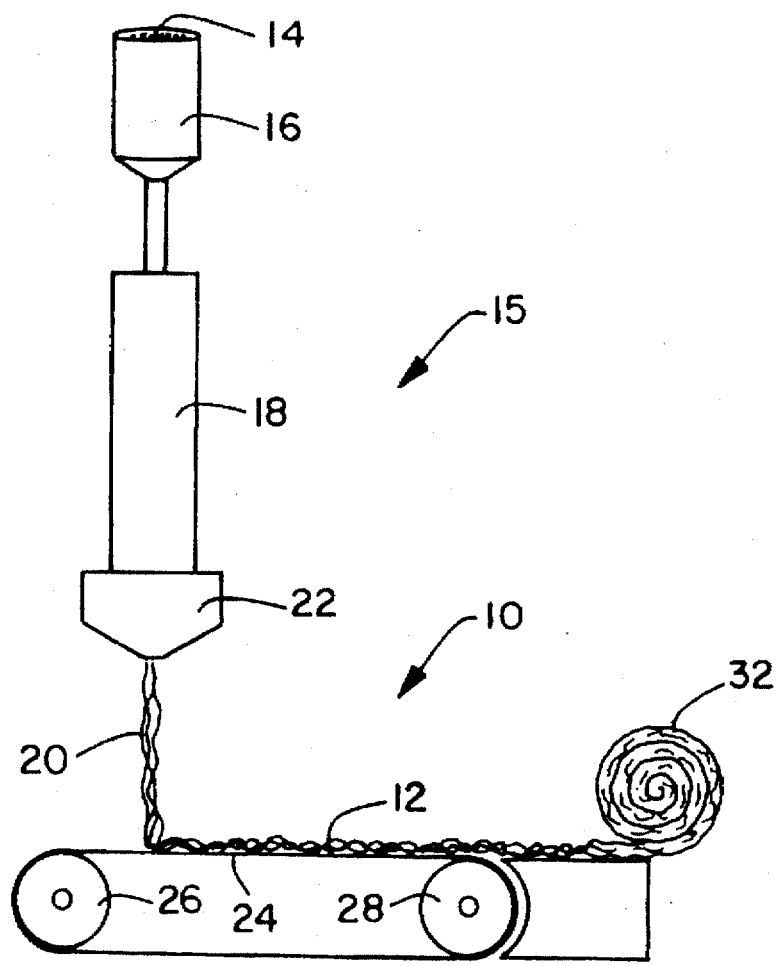
FIG. 1 is a schematic illustration of an exemplary apparatus for manufacturing a nonwoven web of spunbond filaments.

Turning to FIG. 1, there is shown a web forming machine 10 for forming a spunbond web 12 from a plurality of substantially continuous filaments. The web forming machine 10 includes a spunbond station 15 having a supply container 16 which holds a supply of polymer 14. The supply container 16 in the spunbond station 15 feeds into a conventional extruder 18. The polymer is heated and extruded in the form of filaments through a plurality of holes in a spinnerette (not shown). The spun filaments are drawn by means of a take-off device 22.

The drawn, continuous filaments 20 are deposited in a substantially random manner as simple loop springs intertwined on a moving, endless foraminous carrier belt 24 driven over spaced-apart rolls 26 and 28, thereby forming the web 12. As discussed below and, in particular, in Appel et al, U.S. Pat. No. 4,340,563, a spunbond process may be adapted to form such loop springs in response to controllable factors including, for example, filament diameter, filament quench rate, and polymer type. An appropriate suction means (not illustrated) can be present to assist the web formation on the carrier belt 24. The web 12 is formed into a roll 32.

The spunbond station 15 may be a conventional extruder with one or more spinnerettes which form continuous filaments of a polymer and deposit those filaments onto the carrier belt 24 in a random interlaced fashion to form loop springs. The spunbond station 15 may include one or more spinnerette heads depending on the speed of the process and the particular polymer being used. The spunbond station may also be adapted to produce continuous multicomponent filaments. Description of a process of making such multicomponent filaments and a nonwoven fabric composed of such multicomponent filaments may be found in, for example, U.S. patent application Ser. No. 07/933,444, filed on Aug. 21, 1992, and entitled "Nonwoven Multicomponent Polymeric Fabric And Method For Making The Same," now U.S. Pat. No. 5,382,400 the content of which is incorporated herein by reference.

Spunbond materials prepared with continuous filaments generally have at least three common features. First, the polymer is continuously extruded through a spinnerette to form discrete filaments. Second, the filaments are thereafter drawn either mechanically or pneumatically, without breaking, in order to molecularly orient the polymer filaments and achieve tenacity. Third, the continuous filaments are deposited in a substantially random manner onto the carrier belt to form a web.

Conventional nonwoven webs of spunbond filaments generally have filament diameters between about 18 and 25 microns. Conventional webs of such filaments are subsequently bonded (e.g., thermally bonded) to provide a coherent fabric. Filament diameters larger than 25 micron have generally been considered lacking in characteristics desirable for nonwoven webs used in disposable nonwoven fabric applications, and operating conditions are adjusted to reduce or eliminate production of such large diameter spunbond filaments.

As discussed above, one common deficiency of previous attempts to form loop materials of hook and loop fastening systems from conventional thermoplastic filament webs has been inadequate size and/or firmness of the loops so that the hook components do not catch and hold the loop components. That is, loops of inadequate size present too small of a target for the hook elements. Loops of inadequate firmness tend to collapse or get crushed during the fastening step in which hook elements are pressed into the loop material.

According to the present invention, unbonded nonwoven webs made with spunbond filaments having diameters greater than 25 microns and which are arrayed in looping spring configuration are thought to be useful as a loop material in a hook and loop fastening system. These webs are thought to provide satisfactory levels of loop size and/or firmness. Generally speaking, parameters such as the pressure differential in the quench chamber, the polymer flow rate, and the forming distance, are varied according to the polymer being extruded so as to produce the desired filament diameter.

Figure 2:
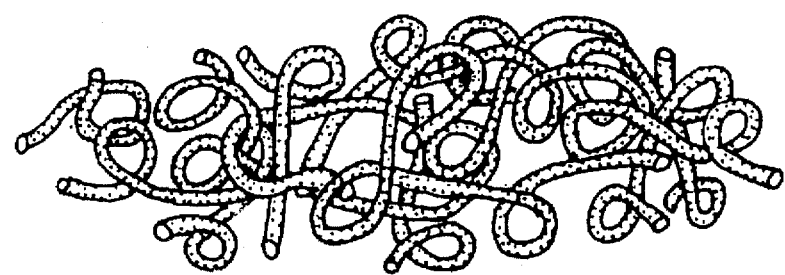
FIG. 2 is a partial section perspective illustration of an exemplary spunbond web.

FIG. 2 is a partial section illustration of the web 12 in perspective view. The discrete, continuous filaments are randomly deposited in simple loops and intertwined in the web. The filaments composing the web 12 are unbonded and free to slide relative to one another.

Figure 3:
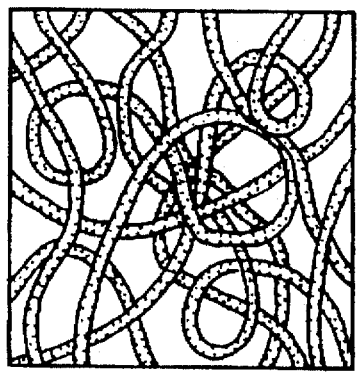
FIG. 3 is an illustration of a planar section of an exemplary spunbond web.
Figure 4:
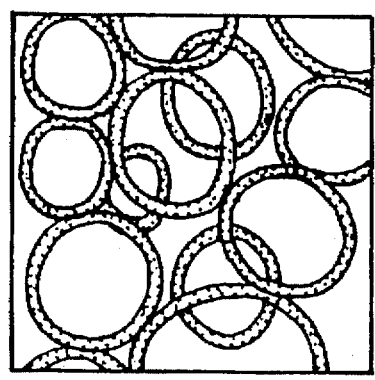
FIG. 4 is an abstraction of the geometry of the filaments forming the web illustrated in FIG. 3.

FIG. 3 illustrates a plane of the web such as that shown in FIG. 2. The filaments are arrayed in the plane of the web as an endless series of simple loops or hitches. By abstraction, this geometry suggests that the spunbond web can be considered to be a collection of circular hoops or springs, as illustrated in FIG. 4. Although the inventors should not be held to a particular theory of operation, it is believed that the circular springs resist deformation.

Figure 5:
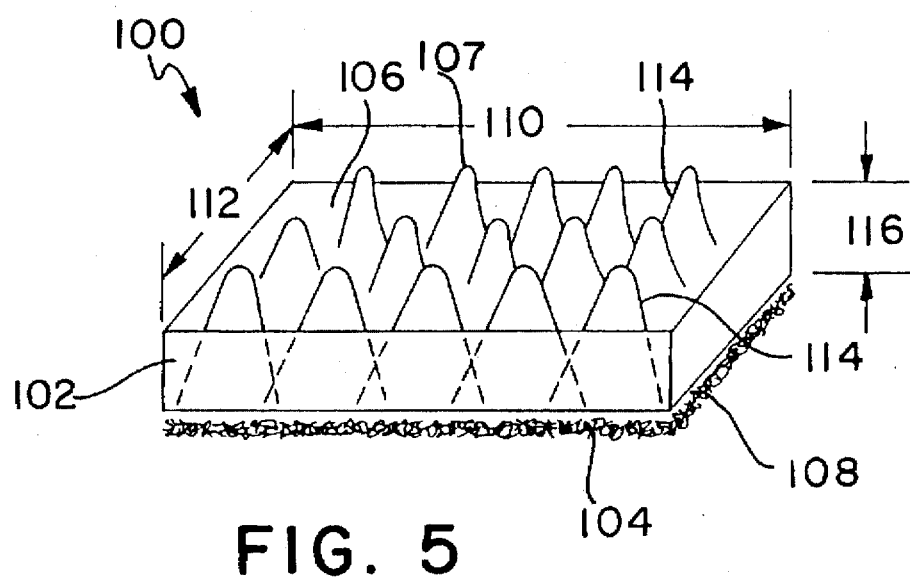
FIG. 5 is a perspective view of a loop material of an exemplary hook and loop fastening system.

Referring to FIG. 5, there is shown a loop material component 100 of a hook and loop fastening system. In its simplest form, the loop material or structure 100 is composed of a backing material 102 and a nonwoven spunbond material 104. The backing material 102 can be made from any number of materials. Desirably, the backing material 102 may be made of a material that has compressive resilience. Alternatively and/or additionally, the backing material 102 may rest on or be attached to a portion of a product that has compressive resilience. Suitable backing materials include, but are not limited to, fibrous nonwoven web materials such as spunbonded, meltblown, air laid, felted and carded webs. Foam materials, both open and closed cell, could also be used with the present invention. Furthermore, combinations of the foregoing materials may be used to achieve varying amounts of strength, resiliency and basis weight. As an example, multi-layered composites may be utilized to form the backing material 102. Typically, the backing material 102 will have a basis weight ranging from about 5 to 100 grams per square meter (gsm). However, the actual basis weight can be varied depending upon the particular end use.

In embodiments where the backing material 102 is a nonwoven fabric, the backing material 102 may be formed from any polymer, or compound, most typically thermoplastic, which is extrudable into fibers. As a means of illustration only, such polymers may include but are not limited to polyolefins, polyesters and polyamides. These polymers, whether used in generally continuous (spunbond, meltblown and tow webs) or staple form (carded webs) usually have fiber diameters ranging from about 1 to 100 microns. However, these diameters may be varied or different diameters and polymers may be combined to meet a particular need. When staple fibers are used, the fiber lengths will generally range from about 5 to 80 millimeters (mm). Furthermore, the fibers may be self-bonded, thermally bonded or chemically bonded to increase the strength of the material. If the backing material 102 has compressive resilience, care should be taken to maintain the compressive resilience when bonding the fibers together.

The backing material 102 may also take the form of a foam, either open or closed cell. Such foams can again, by way of example only, be made from materials including polyurethane and polyethylene. Generally, these foams will have thicknesses ranging from 0.300 to 5 mm.

The backing material 102 may also be a film or film-like material. Films are especially useful in embodiments where the loop material is used as an outer cover for a personal care product. In such an application, the compressive resilience need not be provided solely by the backing. Instead, compressive resilience may be provided by the film and the portion of a product over which the film is located including, for example, an absorbent core, elastic waist bands, elastic leg cuffs or the like.

For example, the loop material could function as a typical loop material for a hook and loop fastening system and also serve as an outer cover of a personal care product. It is contemplated that the loop material could be in the form of a bulked, stretched-pillowed laminate containing at least one extensible layer of film or film-like material (which can function as the backing material) and at least one layer of the spunbond material described above joined together at a plurality of spaced-apart locations.

The backing material 102 has a top surface 106, a bottom surface 108, a length 110 and a width 112. Extending from the bottom surface 108 through the top surface 106 are a plurality of loops 114 formed from the layer of nonwoven spunbond material 104. To form the loops 114 for the present material, a layer 104 of the spunbond material described above is brought in contact with the bottom surface 108 of the backing material 102. Most typically this nonwoven spunbond layer 104 is formed or deposited onto the bottom surface of the backing material 102.

One method of forming a loop material 100 is to form a nonwoven spunbond layer 104 directly onto the surface 108 of the backing material 102. The nonwoven spunbond layer 104 could also be formed independently and brought together with the backing material 102 just before needling or stitchbonding.

Once the loop fibers have been applied to the backing material, they may be needled or stitchbonded through the thickness 116 of the backing material 102 thereby forming a plurality of loops extending from the top surface 106 of the backing material. Such needling may be done by either hydraulic or mechanical means. Typically, flat felt needling loom equipment can be used to form the loops. Such equipment and its use are well known and need not to be disclosed herein in detail. A flat-felt needle loom consists of entry and exit material drive rolls, a reciprocating needle beam, a stripper plate (upper) and a bed plate (lower). The material enters through the entry nip and passes between the stripper plate and a bed plate. The stripper and bed plates are perforated metal surfaces that register according to each needle location on the needle beam. The needle beam reciprocates at 90°, or along the "Z" axis, relative to the plane defined by the plates. On the downward stroke the needle passes through the stripper plate, the nonwoven spunbond material 104, the backing material 102 and finally the bed plate. Barbs on the needles engage the loop material fibers and act to entangle them or, as in this application, push the fibers through the backing material 102. As the needle beam retracts, the fibers are deposited as loops 114 on the top surface 106 of the backing material 102. Loop characteristics, such as loop height and density, are controlled through various needling parameters. Typically, the depth of penetration of the needle through the backing material and the location of the barbs on the needle dictate the loop height. The frequency of the reciprocation of the needle beam, the speed of the materials through the loom, and the density of the needles on the needle beam determine the loop density (expressed as penetrations per square inch or PPI).

Alternatively, a different type of needling equipment can be used for the formation of the loop material of the present invention. This type of needling is referred to as structured needlepunching which is well known and need not be described herein in detail. This type of needle loom shares many similarities with flat felt needling; however, instead of the bed plate used in flat felt needling, a brush belt that moves in the machine direction and at the same speed as the material is used. The brush belt is manufactured to rigorous standards with regard to its density and uniformity. This is a particularly desired method of needling loop materials because the brush maintains the vertical or "Z" axis definition of the loops 114 as being distinct from the top surface 106 of the backing material 102. Also, because the brush belt moves with the material, lighter weight and therefore lower cost materials are possible. In the example discussed below, the material of the present invention was produced on a Dilo Di-Lour II structured needlepunching machine from Dilo Inc. of Charlotte, N.C.

Once the loops 114 have been formed by techniques such as needlepunching and/or stitchbonding, they should be secured to the backing material so that detachment of the hooks 103 will not pull the loops 114 out of the backing material 102. To accomplish this, the portion of the fibers/hooks 114 remaining on or adjacent to the bottom surface 108 of the backing material 102 should be attached thereto. Desirably, the fibers of the nonwoven spunbond material 104 are bonded to the bottom surface 108 of the backing material 102 by such means as adhesives, thermal bonding, ultrasonic bonding or a combination of such means. A wide variety of adhesives will work including, but not limited to, solvent-based, water-based, hot-melt and pressure sensitive adhesives. Powdered adhesives can also be applied to the materials and then heated to activate the powder adhesive and perfect bonding. Typically, adhesive add-ons will be in the range of 10 to 40 mg/in$^2$ (15 gsm to 61 gsm).

In certain situations, simply using as adhesive to bond the fibers/loops 114 of the nonwoven spunbond material 104 to the backing layer 102 may not provide enough strength. As a result, it is possible to add a support layer to the side of the nonwoven spunbond material 104 opposite the backing layer 102 using the same or additional adhesive used to anchor the fibers of the nonwoven spunbond material 104 to the backing layer 102.

If adhesives are used to bond the fibers/loops 114 of the nonwoven spunbond material 104 to the backing layer, it may advantageous to use pressure sensitive adhesives. One advantage is that the pressure sensitive adhesives may also be used to adhere the resultant loop material 100 to another structure such as, for example, the outer cover of a diaper.

However, the easiest method of forming a loop material is to extrusion coat the nonwoven spunbond material 104 described above or thermally laminate a film to the nonwoven spunbond material 104. In order to enhance the bulk and position of the loops, the nonwoven spunbond material could be joined to a film in such a manner as to form a bulked, stretched-pillowed laminate containing at least one extensible layer of film or film-like material (which can function as the backing material) and at least one layer of the spunbond material described above joined together at a plurality of spaced-apart locations to form the laminate which includes a plurality of bonded and unbonded areas.

Such a bulked, stretched-pillowed laminate may be produced by extending a first extensible layer (e.g., a film layer) from an original length to an expanded length with the expanded length being at least 5 percent greater than the original length. Depending upon the degree of stretching, the first extensible layer may be permanently deformed. Next, a second layer of material (e.g., the nonwoven spunbond material described above) is placed in juxtaposition with the first layer while the first layer is still in the expanded length and the two layers are then attached to one another at a plurality of spaced-apart bond sites to form the laminate which includes a plurality of bonded and unbonded areas. Once the laminate has been formed, the first layer is allowed to relax to a third length which is usually longer than the first length of the first layer. As a result of the attachment of the second layer to the first layer while the first layer is in an expanded state, once the laminate contracts, the first layer gathers and puckers, thereby forming a much bulkier material as compared to a simple non-stretched laminate of the same two materials.

In other words, one of the layers (e.g., the film) is stretched and in some cases permanently deformed from a first or original length L1 to a second length L2 which is greater than its original length. After the first layer has been stretched, and while it is still in a tensioned condition, a second layer (e.g., the nonwoven spunbond material) is attached to the first layer. Due to the nature of the stretching of the first layer, the first layer still has some degree of recovery. As a result, after the two layers have been attached to one another, the tension is released and the layers are allowed to retract slightly to a third length L3 which is greater than the first or original length L1 of the first layer yet slightly less than the second, stretched length L2 of the first layer. Due to the slight recovery of the first layer, the second layer tends to gather and form pillows thereby imparting a bulky, more three-dimensional appearance to the composite. This is because the second layer has a larger surface area than the first layer per the same unit area of the composite. Of course, the laminate should not be limited to just two layers. It is contemplated that more than two layers may easily be used to construct multilayer laminates.

Generally speaking, the second layer is composed of the nonwoven spunbond material. It is thought that by gathering, forming pillows and otherwise increasing the surface area of the second layer, the intertwined loop springs of spunbond material will be positioned (i.e., "presented) in a manner that enhances penetration by mechanical hooks and which promotes engagement by mechanical hooks of a hook and loop fastening system.

Attachment of the various layers to one another can be accomplished by a variety of means including adhesives, ultrasonic bonding, thermo-mechanical bonding, stitching, etc. Suitable adhesives include water-based, solvent-based, pressure-sensitive, and hot-melt adhesives.

Extension of the first layer can be from as little as 5% to as much as 1200% of the original length of the first layer. Usually, when stretching the first layer several hundred percent or more, the first layer will permanently deform such that upon relaxation of the stretching forces, the first layer only retracts a small portion of the distance that the first layer was initially stretched. As a result, the retracted or third length may be, for example, between about 80 and 98% of the expanded length.

Referring to FIG. 5, the distance between the top surface 106 and the apexes 107 of the loops 114 should be between about 1 and 10 mm. When the engagement of the hooks with the loops takes place, the hooks first encounter the apexes 107 of the loops that have maintained an upstanding orientation due to the supporting effect of the backing material, especially if the backing material is a resilient backing material or if the nonwoven spunbond material has been bulked, pillowed and gathered as described above. This "presentation" of the loops to the hook, in itself, increases the number of hooks/loop engagements. Further, the hook apexes impinging on the backing may compress the backing material along the "Z" axis of the material (especially if the a resilient backing is used), such that more of the loop structure is exposed and available for engagement. The compressional recovery characteristic of resilient backing materials provides for desirable "rebounding" after engagement which serves to promote the "locking" of fibers that have engaged hooks resulting in elevated shear and peel values.

Figure 6:
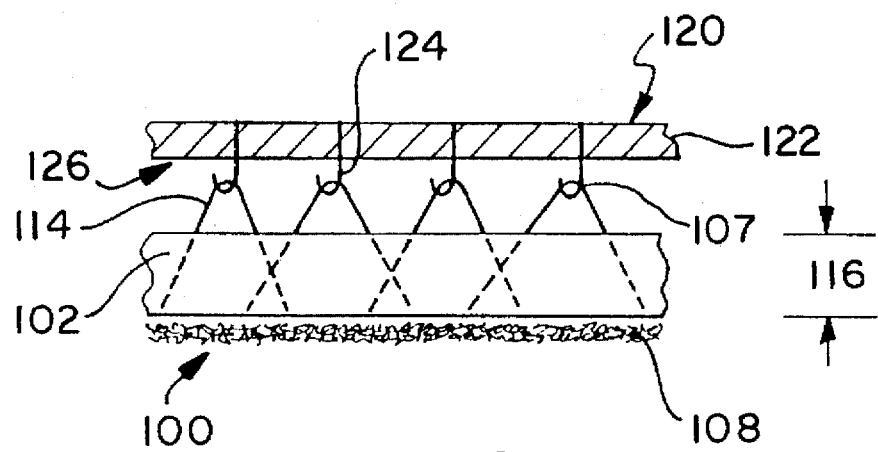
FIG. 6 is a cross-sectional view of a loop material engaged with hook elements of an exemplary hook and loop fastening system.

Referring to FIG. 6, there is shown a cross-sectional view of a loop material 100 (as depicted in FIG. 5) fully engaged with hook elements in an exemplary hook and loop fastening system. The hook material 120 includes a base layer 122 with a plurality of hook members 124 extending generally perpendicularly therefrom. The hook members 124 have an average overall height measured from the top surface 126 of the base material 122 to the highest point on the hook members 124. An exemplary hook material 124 may be obtained from Velcro, USA of Manchester, N.H. as Telcar 102 Hook #15. The material comes in 4-inch widths and has an average height of about 0.889 millimeters (mm).

Nonwoven spunbond webs will be described in connection with the following examples. These nonwoven spunbond webs were prepared to contain a plurality of continuous intertwined filaments, each having a diameter of about 25 to about 100 microns, the plurality of filaments laid randomly to define a plurality of intertwined loop springs, each having a diameter of about 0.5 to about 3 millimeters.

In the examples, the webs were converted into filter rods and measured to determine pressure drop and firmness. As is later shown, those specific properties are believed to be dependent on the nature of the nonwoven spunbond web having the intertwined loop springs. Although the following example relates to a filter rod application, the data and analysis directs attention to the basic feature of the nonwoven spunbond web—its intertwined loop springs having certain recited dimensions. As is clear from the preceding discussion, the nonwoven spunbond web with its intertwined loop springs having certain recited dimensions has application as a loop material for a hook and loop fastening system as well as a filter material. Accordingly, it will be understood that the following examples are not intended to limit the invention to those embodiments. On the contrary, it is intended to cover all alternatives, modifications and equivalents as may be included within the spirit and scope of the invention as disclosed in the preceding discussion and as defined by the appended claims.

EXAMPLES

Sample spunbond webs were made using an Exxon commercial grade polypropylene polymer. The webs were manufactured generally in accordance with the teachings of previously referenced U.S. Pat. No. 4,340,563 utilizing a linear drawing system apparatus having a 400 hole die pack. The inlet melt temperature was about 425° F. and throughput was about 0.8 grams of polymer per hole per minute. The die pack temperature was about 430° F. The web basis weight was about 0.8 ounces per square yard (osy) (about 27 grams per square meter). Different filament diameters were obtained by changing the duct pressure differential in the quenching chamber.

Filter rods were made from the 0.8 osy (27 gsm) unbonded webs with filament diameters ranging from about 17 to about 39 microns using conventional cigarette filter rod making equipment. The filters were wrapped with a non-porous plug wrap having the trade designation SPW-310 available from Kimberly-Clark Corporation. Filter weight, firmness, and pressure drop tests were conducted on the filters to evaluate the performance of the loop springs of the spunbond web. Each test is described below.

As used herein, the term "filter weight" refers to the measure of the mass of web incorporated into an individual filter. Filter weight is reported as net filter weight (NFW) in units of milligrams per centimeter of filter length minus the weight of the plug wrap paper. Generally speaking, when the materials of the present invention are used in such applications as conventional cigarette filters, the filter weights tend to be less than 80 mg per cm of filter length.

As used herein, the term "firmness" refers to the deflection of a deformable material (e.g., a cigarette filter rod) in response to an applied force. More particularly, the firmness of cigarette filter samples was measured using an Eastman Firmness Gauge (available from Eastman Chemical Products, Inc., Kingsport, Tenn., division of Eastman Kodak Company). This instrument applies a weight of 350 grams to a test filter. The weight was applied through the shaft of a dial indicator (available from the Federal Products Company, Providence, R.I.) to a circular foot having a diameter of about ½ inch (12.5 millimeters) positioned directly on the filter. The filter is placed below the foot which is lowered to contact the sample without the 350 gram weight being applied to the test filter. The dial indicator is adjusted to have the needle pointing to scale 0. The 350 gram weight is released by an off-set cam and applied to the filter. A reading of the Federal dial is taken after 5 seconds to determine the number of tenths of millimeter deflection. A reading of 10.0 means the test filter has been depressed 1.0 millimeter by the 350 gram weight. Generally speaking, a test result of between about 3 to 8 (i.e., 0.3 to 0.8 millimeter deflection) is a desirable range for cigarette filters. More desirably, the test result is between 4 to 8 (i.e., 0.4 to 0.8 millimeter deflection).

As used herein, the term "filter pressure drop" refers to the amount of vacuum (expressed in centimeters of water) required to draw approximately 1050 cm$^3$/min of air through the filter. Generally speaking, the pressure drop is expressed in centimeters of water and may be normalized to unit length of filter by dividing by the actual filter length. In accordance with the invention, the pressure drop of a filter is desirably in the range of 1.0 to 4.5 cm water/cm filter length. More desirably, the pressure drop is in the range of from about 1.5 to 3.5 cm water/cm filter length.

Circumference of the each filter was measured with a Filtrona Model MTG 102 Tape Gauge available from Fidus Instruments Corporation of Richmond, Va.

Table 1 below reports the test results of the cigarette filter made from the spunbond webs having filament diameters ranging from 17–39 microns as described above. The net filter weight (NFW) is reported in milligrams per centimeter of filter length (minus the filter wrap). The pressure drop is reported in centimeters of water per centimeter of filter length. The firmness is reported as millimeters of deflection.

TABLE 1

| Sample | Filament Diameter (microns) | Plug Wrap | NFW (mg/cm) | Press Drop* | Firm | Circ. (mm) |
| --- | --- | --- | --- | --- | --- | --- |
| A | 16–17 | SPW-310 | 75 | 8.9 | 4.7 | 24.4 |
| B | 22–23 | SPW-310 | 71 | 5.1 | 7.8 | 24.4 |
| C | 24–25 | SPW-310 | 70 | 3.8 | 7.6 | 24.4 |
| D | 29–30 | SPW-310 | 71 | 3.5 | 7.2 | 24.2 |
| E | 38–39 | SPW-310 | 73 | 2.2 | 7.3 | 24.2 |

*cm of water/cm of filter length

Based on the data in Table 1, it is expected that samples C, D & E would provide a spunbond web with intertwined loop springs having adequate firmness for a loop material of a hook and loop fastener system. Plug A & B exhibit a higher level of pressure drop. It is thought that a higher level of pressure drop may provide lower levels of firmness for the loop springs of the spunbond web and might prove unsatisfactory for a loop material in a hook and loop fastening system.

While it is not desired to limit the invention to any particular theory, one possible explanation for the resulting desirable plug firmness and pressure drop may be understood by considering that the spunbond filaments comprising the web behave as a collection of circular hoops or springs such as illustrated in FIG. 4. When such a web is reconfigured to make a filter rod, the resistance to deformation of these circular springs prevents collapse of the filter.

It is known from mechanics that the resistance to deformation or stiffness (S) of such springs is proportional with the fourth power of the filament diameter (d) and inversely proportional with the third power of the circular spring diameter (D), i.e., $$S = k\, d^4/D^3 \qquad \text{(Eq. 1)}$$

where k is a proportionality constant which incorporates the filament modulus of the particular polymer used.

Considering that most of the spring diameters (D) are roughly constant in the spunbond webs, this factor can be grouped with the constant k in equation (1) to yield the simple stiffness equation:

$$S = k'\, d^4 \qquad \text{(Eq. 2)}$$

Equation 2 may then be applied to the unbonded webs A through E of Table 2 by dividing each filament diameter by the smallest filament diameter (web A) to yield a normalized diameter. When this is done, a stiffness enhancement can be calculated by merely raising these normalized diameters to the fourth power. The results are shown below.

TABLE 2

| Unbonded Web | Filament Diameter (microns) | Normalized Filament Diameter | Stiffness Enhancement |
| --- | --- | --- | --- |
| A | 17 | 1 | 1 |
| B | 22 | 1.29 | 2.80 |
| C | 25 | 1.47 | 4.68 |
| D | 30 | 1.77 | 9.7 |
| E | 38 | 2.24 | 24.9 |

Such spring analysis can be useful in predicting the behavior of fiber/filament tows used to make conventional cigarette filters. Generally speaking, fiber/filament tows having a high degree of machine direction (MD) orientation are unlikely to have identifiable spring-like structures, much less spring-like structures characterized by relatively uniform small diameters [i.e., if any spring-like structures are present, they are likely to be of very large diameter (D)]. When this information is substituted in Equation 1, the stiffness of the spring structures is calculated to be low because the value of the third power of the circular spring diameter in the denominator would be very large.

Although the inventors should not be held to a particular theory of operation or practice, it is believed that in the manufacture of nonwoven spunbond webs of the present invention, the continuous spunbond filaments should not be "drawn out" by excessive draws in the forming section of the spunbond process. Avoiding excessive draws will generally prevent destruction of the circular spring-like structures (having relatively uniform small diameters) present in the spunbond web produced in accordance with the present invention.

It is contemplated that any thermoplastic polymer suitable for spunbond processing may be used in the practice of the present invention. Desirably, the nonwoven web may be formed from polyesters, polyamides or polyolefins. Exemplary polyolefins include polyethylene, polypropylene, polybutene, ethylene copolymers, propylene copolymers and butene copolymers. More desirably, the polyolefin is isotatic polypropylene.

Due to the nature of the spunbond thermoforming process, additives (e.g., calcium carbonate) can be easily incorporated internally in the polymer or blown onto the molten polymer surface as the polymer is extruded, in order to change the structure of the spunbond web and thus its performance in a filter element. Also, spunbond webs, after formation, are easily subject to known post treatments with auxiliary agents in dry or liquid form to provide certain desired attributes.

While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What is claimed is:

1. A loop material for a hook and loop fastening system comprising:
   a backing material; and
   a layer of a nonwoven spunbond web attached to the backing material and having a loop material surface, the nonwoven spunbond web comprising a plurality of continuous intertwined filaments, each having a diameter of about 25 to about 100 microns, the plurality of filaments laid randomly to define a plurality of intertwined loop springs tending to maintain a "z" axis orientation 90° from said loop material surface, each of said plurality of springs having a diameter of about 0.5 to about 3 millimeters.

2. The loop material of claim 1, wherein the filaments have a diameter of about 25 to about 40 microns.

3. The loop material of claim 1, wherein the plurality of intertwined loop springs each have a diameter of about 1 to 2 millimeters.

4. The loop material of claim 1, wherein the filaments are formed from a thermoplastic polymer selected from polyolefins, polyamides and polyesters.

5. The loop material of claim 4, wherein the filaments are formed from a thermoplastic polyolefin polymer selected from polyethylene, polypropylene, polybutene, ethylene copolymers, propylene copolymers and butene copolymers.

6. An outer cover for a personal care absorbent product, the outer cover comprising a loop material composed of a backing material and a layer of a nonwoven spunbond web as recited in claim 1.

7. The outer cover of claim 6, wherein the backing material is a layer of film.

8. The outer cover of claim 7, wherein at least one layer of film and at least one layer of a nonwoven spunbond web as recited in claim 1 are joined together at a plurality of spaced-apart locations in the form of a bulked, stretched-pillowed laminate.

9. An outer cover for a personal care absorbent product, the outer cover comprising a loop material composed of a backing material and a layer of a nonwoven spunbond web having a loop material surface, the spunbond web comprising a plurality of continuous intertwined filaments, each having a diameter of about 25 to about 100 microns, the plurality of filaments laid randomly to define a plurality of intertwined loop springs tending to maintain a "z" axis orientation of about 90° from said loop material surface, each of said plurality of springs having a diameter of about 0.5 to 3 millimeters.

10. The outer cover of claim 9, wherein the backing material is a layer of film.

11. The outer cover of claim 9, wherein filaments have a diameter of about 25 to about 40 microns.

12. The outer cover of claim 9, wherein the plurality of intertwined loop springs each has a diameter of about 1 to 2 millimeters.

13. The outer cover of claim 9, wherein the filaments are formed from a thermoplastic polymer selected from polyolefins, polyamides and polyesters.

14. The outer cover of claim 13, wherein the filaments are formed from a thermoplastic polyolefin polymer selected from polyethylene, polypropylene, polybutene, ethylene copolymers, propylene copolymers and butene copolymers.

15. The outer cover of claim 10, wherein at least one layer of film and at least one layer of the nonwoven spunbond web are joined together at a plurality of spaced-apart locations in the form of a bulked, stretched-pillowed laminate.

16. A nonwoven spunbond web adapted to form a loop material for a hook and loop fastening system, the web having a loop material surface and comprising a plurality of continuous intertwined filaments, each having a diameter of about 25 to about 100 microns, the plurality of filaments laid randomly to define a plurality of intertwined loop springs tending to maintain a "z" axis orientation of about 90° from said loop material surface, each of said plurality of springs having a diameter of about 0.5 to about 3 millimeters.

\* \* \* \* \*

UNITED STATES PATENT AND TRADEMARK OFFICE
CERTIFICATION OF CORRECTION

PATENT NO. : 5,669,900                           Page 1 of 4

DATED : September 23, 1997

INVENTOR(S): Bullwinkel et al.

It is certified that errors appear in the above-identified patent and that said Letters Patent is hereby corrected as shown below:

On the title page;

Page 1 [56] References Cited, U.S. PATENT DOCUMENTS, add:
-- 439,004    10/1890    Harris--;
--2,966,157   12/1960    Touey et al.--;
--3,110,642   11/1963    Harrington--;
--3,226,795    1/1966    Swerdloff--;
--3,276,944   10/1966    Levy--;
--3,318,632    5/1967    Struble et al.--;
--3,329,544    7/1967    Smith et al.--;
--3,338,992    8/1967    Kinney--;
--3,341,394    9/1967    Kinney--;
--3,393,685    7/1968    Mumpower, II--;
--3,396,733    8/1968    Allseits et al.--;
--3,407,822   10/1968    Touey et al.--;
--3,461,882    8/1969    Epstein--;
--3,502,538    3/1970    Petersen--;
--3,502,763    3/1970    Hartmann--;
--3,509,009    4/1970    Hartmann--;
--3,538,920   11/1970    Davis--;
--3,542,615   11/1970    Dobo et al.--;
--3,595,245    7/1971    Buntin--;
--3,608,564    9/1971    Takahashi--;
--3,692,618    9/1972    Dorschner et al.--;
--3,694,867   10/1972    Stumpf--;
--3,749,685    7/1973    Johnson, Jr.--;
--3,849,241   11/1974    Butin et al.--;
--3,856,025   12/1974    Sato--;
--3,861,404    1/1975    Changani--;

UNITED STATES PATENT AND TRADEMARK OFFICE

CERTIFICATION OF CORRECTION

PATENT NO. : 5,669,900          Page 2 of 4

DATED       : September 23, 1997

INVENTOR(S): Bullwinkel et al.

It is certified that errors appear in the above-identified patent and that said Letters Patent is hereby corrected as shown below:

```
--3,880,173    4/1975     Hill--;
--3,882,877    5/1975     Brackmann--;
--3,887,730    6/1975     Rainer--;
--3,930,077    12/1975    Levers et al.--;
--3,939,849    2/1976     Baxter--;
--3,978,185    8/1976     Buntin--;
--4,054,550    10/1977    Parker--;
--4,056,281    11/1977    Byrnes--;
--4,059,121    11/1977    Brackmann--;
--4,182,350    1/1980     Steinau--;
--4,232,130    11/1980    Baxter--;
--4,279,848    7/1981     Baxter et al.--;
--4,340,563    7/1982     Appel et al.--;
--4,364,403    12/1982    Horsewell et al.--;
--4,366,826    1/1983     Horsewell--;
--4,379,465    4/1983     Coq--;
--4,389,442    6/1983     Pickens, Jr. et al.--;
--4,546,040    10/1985    Knotek--;
--4,739,635    4/1988     Conley et al.--;
--4,761,318    8/1988     Ott et al.--;
--4,770,917    9/1988     Tochacek et al.--;
--4,776,068    10/1988    Smirlock et al.--;
--4,861,399    8/1989     Rajala et al.--;
--4,931,343    6/1990     Becker et al.--;
--4,961,415    10/1990    Radwanski et al.--;
```
Page 1 [56] References Cited, FOREIGN PATENT DOCUMENTS, add:
--10962/88     1/1988     Australia--;

UNITED STATES PATENT AND TRADEMARK OFFICE

CERTIFICATION OF CORRECTION

PATENT NO. : 5,669,900

DATED : September 23, 1997

INVENTOR(S): Bullwinkel et al.

It is certified that errors appear in the above-identified patent and that said Letters Patent is hereby corrected as shown below:

```
--803714    1/1969    Canada--;
--210536    2/1990    European Pat. Off.--;
--258015    3/1988    European Pat. Off.--;
--276890    8/1988    European Pat. Off.--;
--276970    8/1988    European Pat. Off.--;
--278866    8/1988    European Pat. Off.--;
--289198    11/1988   European Pat. Off.--;
--888943    11/1988   South Africa--;
--2233876   1/1991    United Kingdom--;
--9201401   2/1992    WIPO--;
```

Page 1 [56] References Cited, OTHER PUBLICATIONS, add:

--Japanese Abstract JP 63 145 462 dated Jun. 17, 1988.--;

--NRL Report 4364, "Manufacture of Superfine Organic Fibers", V.A. Wente, E.L. Boone, C.D. Fluharty, May 25, 1954, pp. 1-15.--;

--NRL Report 5265, "An Improved Device for the Formation of Super-Fine Thermoplastic Fibers", K.D. Lawrence, R.T. Lukas, J.A. Young.--;

UNITED STATES PATENT AND TRADEMARK OFFICE
CERTIFICATE OF CORRECTION

PATENT NO.  : 5,669,900
DATED       : September 23, 1997
INVENTOR(S) : Bullwinkel et al.

It is certified that error appears in the above-identified patent and that said Letters Patent is hereby corrected as shown below:

Column 7, line 26, "may advantageous" should read --may be advantageous--;
Column 8, line 52, "if the a" should read --if a --;
Column 10, line 30, "of the each" should read --of each--;
Column 12, line 60, "0.5 to 3" should read --0.5 to about 3--.

Signed and Sealed this

Seventeenth Day of November, 1998

Attest:

BRUCE LEHMAN

Attesting Officer

Commissioner of Patents and Trademarks